Figure 1:
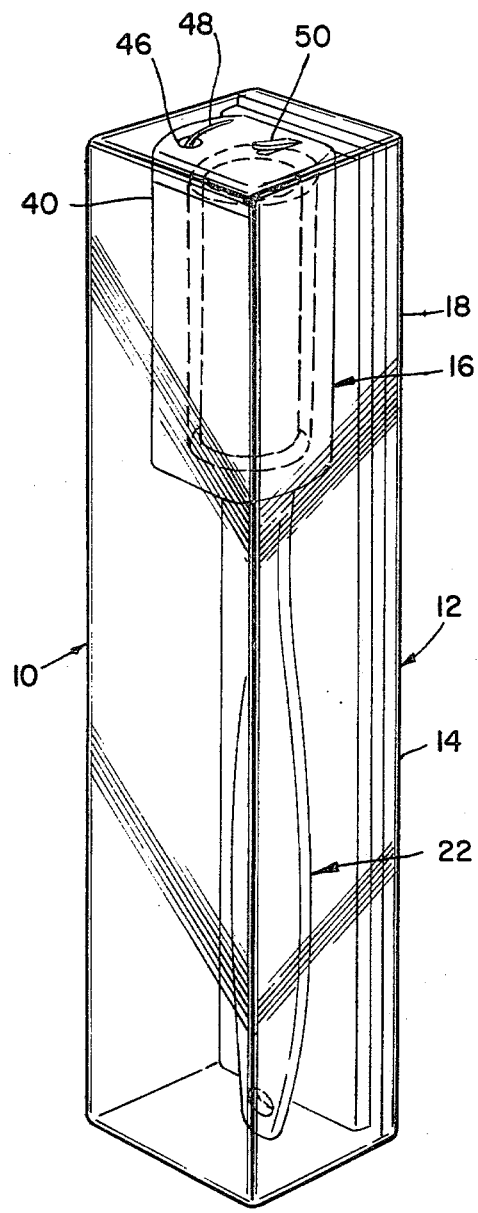

United States Patent [19]

Talbot

[11] 4,286,611
[45] Sep. 1, 1981

[54] DENTAL FLOSS DISPENSER

[76] Inventor: Patricia A. Talbot, 44 Fulton St., Norwood, Mass. 02062

[21] Appl. No.: 121,322

[22] Filed: Feb. 14, 1980

[51] Int. Cl.³ .............................................. A61C 15/00
[52] U.S. Cl. ..................................................... 132/91
[58] Field of Search .................................. 132/89–93, 132/84 D

[56] References Cited

U.S. PATENT DOCUMENTS

| | | | |
|---|---|---|---|
| 1,213,235 | 1/1917 | Meiers | 132/84 D |
| 1,427,857 | 9/1922 | Satterlee | 132/92 R |
| 2,029,031 | 1/1936 | Novick | 132/91 |
| 3,913,597 | 10/1975 | Day | 132/92 R |
| 3,949,769 | 4/1976 | Minka | 132/91 |

Primary Examiner—G. E. McNeill
Attorney, Agent, or Firm—Robert R. Churchill

[57] ABSTRACT

The present invention relates to a novel and improved dental floss dispenser and a container for the same.

The dispenser consists of a body portion adapted to carry a spool of dental floss and has means at one end thereof for enabling lengths of the floss to be withdrawn from the body portion for use. The dispenser has a novel removable handle removably secured at the other end of the body portion. The entire dispenser is shaped in the manner of a tooth brush and the container is preferably clear or translucent and shaped similarly to that of a tooth brush container.

4 Claims, 4 Drawing Figures

DENTAL FLOSS DISPENSER

BACKGROUND OF THE INVENTION

The invention resides in the field of dental floss dispensers and containers for the same.

DESCRIPTION OF THE PRIOR ART

Prior to the present invention substantially all of the dental floss packages of which I am aware consist of a round spool of dental floss inserted in some type of conventional container which must be secured to a card in order for it to be displayed in a drug store or the like. Other types of packages are available, but none of which is capable of being displayed easily and practically in the oral needs department of the store. As a result of this unmanageable packaging situation "out of sight" as well as "out of stock" problems are created. In essence carded items by virtue of their unusual shapes cannot conform to the generally accepted standards of consumer packaged goods. The product because of its peculiar dimensions "floats" into other areas of the department store other than the oral hygiene section and cannot be easily found by the customer, if found at all. As a result the potential loss of floss sales is tremendous since customers cannot and will not spend excessive amounts of time in searching for products within a store. The present invention provides a dispenser capable of being easily packaged and displayed with other dental products and which is adapted for location in the home in a standard tooth brush fixture of the type having a series of openings which enable the toothbrush handle to be inserted and the brush to hang therein.

FIELD OF THE INVENTION

The present invention has for a principal object to provide a novel and improved dental floss dispenser and package for the same whereby the availability of and use of the dental floss is substantially increased.

Another object of the invention is to provide a novel and improved dental floss dispenser which is characterized by a novel structure enabling it to be stored in the bathroom on an ordinary tooth brush fixture.

A further object of the invention is to provide a novel and improved dental floss dispenser characterized by novel structure wherein it can be readily displayed in the oral needs department of a store on conventional tooth brush racks or shelves wherein tooth brushes are being displayed.

A still further object of the invention is to provide a novel and improved dental floss dispenser of a uniform size and shape to greatly facilitate merchandising of the same.

DRAWINGS

Figure 3:
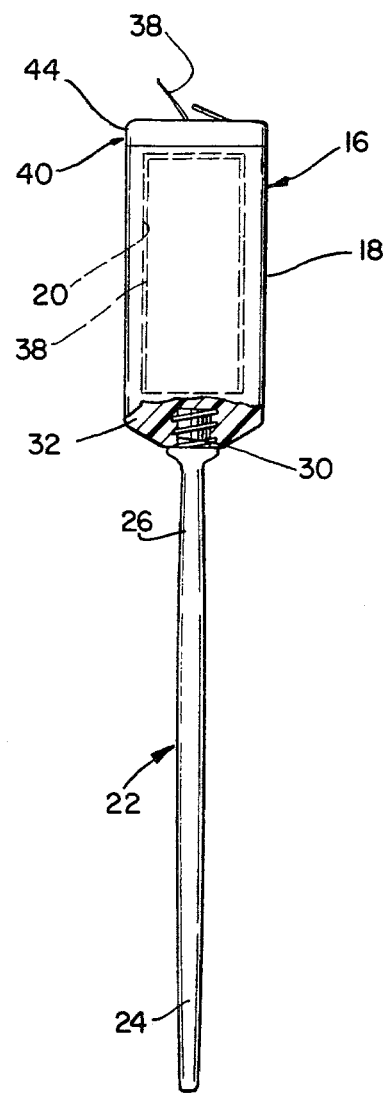
Figure 4:
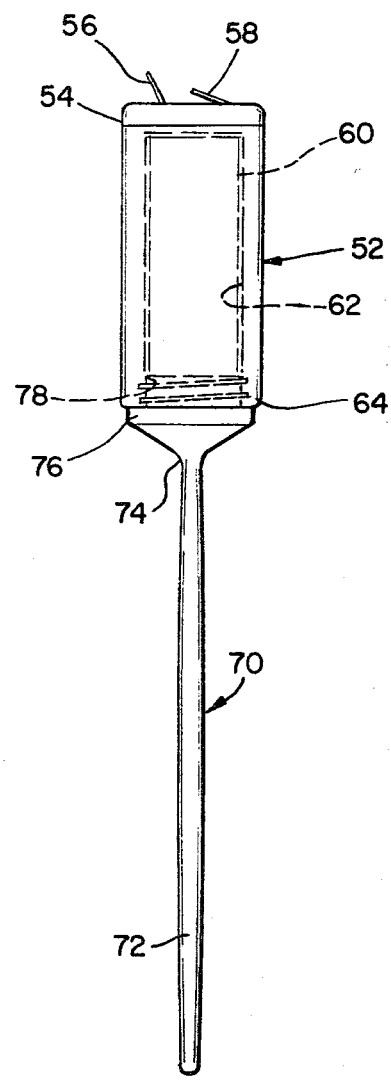

In the drawings illustrating the present invention:
FIG. 1 is a vertical front view of the preferred form of the present invention,
FIG. 2 is a view of the dispenser partially in cross-section showing the removable handle in operative position,
FIG. 3 is a side elevation of the dispenser of FIG. 2 illustrating the handle structure, and
FIG. 4 is a side elevation of another form of the present invention illustrating another form of the removable handle structure.

SUMMARY OF THE INVENTION

Referring now to the drawings illustrating the preferred embodiment of the present invention, and to FIG. 1 in particular illustrating the present novel and improved invention. As shown 10 illustrates an elongated clear plastic rectangular container open at one side 12 and having a snugly fitted cover 14 for the open side 12. As illustrated the present dispenser 16 is constructed to be similar in its general shape to that of a tooth brush for reasons to hereinafter be more fully described.

Figure 2:
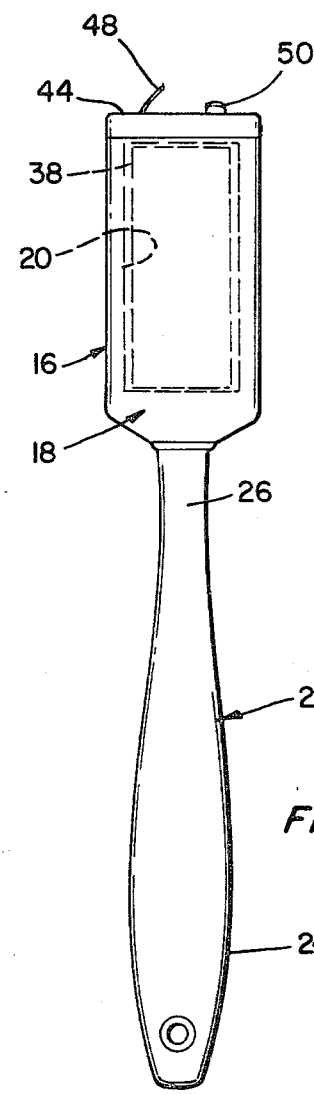

FIG. 2 illustrates the preferred form of the present invention. The dispenser consists of an enlarged body or floss holding portion 18 having a hollow cavity 20 and a removable handle 22. The handle, as shown, is similar in shape to that of a conventional tooth brush in that it has an enlarged rather flat holding portion 24 tapering into a narrow neck portion 26. The handle is removably secured to the lower end of the dispenser body portion 18, as shown in FIGS. 2 and 3. The narrow end 28 is threaded, as illustrated, and is adapted to be inserted into a threaded aperture 30 in the bottom portion 32 of the dispenser.

The handle receiving bottom portion 32 of the dispenser is solid and has a centrally located threaded opening 30 into which the handle 22 is arranged to be screwed whereby it is firmly attached to the dispenser. This structure is best shown in FIGS. 2 and 3.

The end 24 of the handle 22 is provided with a hole 36 which enables the dispenser to be hung on a tooth brush holder in the bathroom beside the family toothbrushes. This enables the dental floss to be readily available for use and since it is so handy to the other dental products, increases its use so necessary to good dental hygiene.

In each form of the invention herein illustrated the dental floss 38 is cylindrically wound in conventional tubular form and is inserted into the cavity 20 and held loosely therein so that lengths may be withdrawn for use.

Referring now to the body portion 18 of the form of the invention illustrated in FIGS. 1 thru 3,
The upper end 40 of the body portion 18 is open for access into the cavity 20. The cylinder of dental floss 38 is inserted into the cavity 20 through the opening 42 and positioned therein as shown. A cover 44 is provided for the open end of the dispenser 16. An opening 46 is formed in the top of the cover 44 through which a thread 48 of the floss is drawn and a sharp edged flap 50 is also formed in the cover in spaced relation to the opening 46 through which the thread is drawn.

A portion of the opposed end 32 of the body portion of the dispenser is solid and includes the threaded opening 30 arranged to receive the correspondingly threaded end 28 of the handle so that it can be screwed tightly into place and attached to the floss holding body portion of the dispenser. Thus the dispenser is provided with a handle to facilitate use of the dispenser in removing dental floss therefrom for use.

In operation a length of the floss is withdrawn from the floss cylinder 38 through the opening 46 and is brought into engagement with the sharp edge of the flap 50 thereby is severed by the pressure against the sharp edge of the flap and is ready for use.

As heretofore described the cylinder of floss fits loosely enough within the cavity so that it may rotate as the thread of floss is withdrawn as described.

As may be easily understood whenever necessary or desirable the size of the present dispenser may be reduced by simply removing the handle. This would be advantageous when packing the dental goods for traveling or in cases wherein a smaller unit is desirable.

FIG. 4 illustrates a modified form of the present invention wherein the dispenser consists of a similar floss holding body portion 52 having a top portion 54 provided with a floss opening 56 and a cutting edge 58 for cutting off lengths of floss for use.

A roll of dental floss 60 similar to that of FIGS. 1–3 is loosely inserted into cavity 62 in portion 52 of the dispenser. The lower end 64 of the body portion is open and permits insertion of the floss 60 into the body portion, as shown.

A handle 70 having a flat relatively wide hand holding end 72, a narrow neck portion 74, and flat cyclindrical flange 76 is arranged to be removable secured to the body portion after the floss is inserted into the cavity 62. The flange 76 is threaded and is arranged to be screwed into threaded portion 78 at the open end of the body portion as shown.

In operation the floss may be withdrawn and the desired length cut off in the same manner as heretofore described in connection with the form of the invention illustrated in FIGS. 1–3 and similarly the handle 70 may be removed by merely unscrewing the same from the floss holding body portion.

In this form of the invention the floss is fed into the body portion when the handle is removed and held in place when the handle is again secured to the body portion.

While in this form of the invention the handle is described as being screwed into a plurality of threads in the body portion to maintain it in operative position, it will be understood that the lower end of the body portion may be provided with a slot such that when the end of the handle is inserted into the opening a single turn or half turn would lock it securely in position.

From the foregoing description it will be apparent that while the present novel and improved dental floss dispenser is relatively simple in structure it is highly efficient in use. The present dispenser enables not only the floss to be readily and properly displayed in the oral needs department of the store so that the purchasing public is made more conscious of the floss and its importance to oral hygiene and dental care, but also its novel structure permits its storage in the home bathroom to be on the same fixture as are the family tooth brushes. It will be apparent that this is highly important in increasing the use of dental floss so necessary in preventative dentistry and in keeping with most dentist's "brush and floss" policy.

It will also be apparent from the foregoing description that the present novel and improved dispenser provides a structure which greatly facilitates shelving and housing of dental floss as an item in the retail store trade. It permits or facilitates the allocation of specific space to the dental floss category, allows for better inventory control, reduces "out of stocks" common to "carded items" as well as enabling more exact rate of sale to be determined for the category. Most important of all it enables the item, dental floss, to be located right in the tooth brush section in the store.

In addition, the removable handle makes the dispenser even more versatile, by in the preferred form of the invention, enabling it to be quickly reduced in size for traveling or in general, more readily portable.

From the foregoing description it will be understood that while the preferred embodiment of the invention has been illustrated and described certain changes and modifications may be made without departing from the scope of the present invention.

Having thus described the invention what is claimed is:

1. In combination, a dental floss dispenser and a container for the same, said dispenser comprising a hollow cylindrical body portion, and a handle detachably secured to one end of the body portion having a removable cover, a spool of dental floss mounted within the hollow body portion and means in said cover for permitting a length of floss to be withdrawn therefrom and cut off for use.

2. A dispenser as defined in claim 1, wherein the handle is shaped similar to a toothbrush handle.

3. A dispenser as defined in claim 1, wherein the lower end of the body portion is provided with a threaded opening and one end of the handle is threaded such that it is adapted to be screwed into the threaded opening in said body portion and securely and removably attached to the body portion.

4. A dental floss dispenser adapted for storage on a bathroom fixture comprising of a hollow cylindrical body portion having an open end and a closed end and a handle for the same arranged to be detachably secured to the open end of said body portion, a spool of dental floss mounted within the hollow body portion, small opening and a cutting surface disposed in the closed end of said body portion to enable the dental floss to be withdrawn from the dispenser and cut to desired lengths for use.

* * * * *